United States Patent
Romano

(10) Patent No.: US 9,198,418 B2
(45) Date of Patent: Dec. 1, 2015

(54) **HIGH ACTIVITY ANTIPARASITIC COMPOSITION AGAINST *RHYNCHOPHORUS FERRUGINEUS***

(75) Inventor: Giuseppe Romano, Ehrendingen (CH)

(73) Assignee: ROMANO NATUR GMBH, Ehrendingen (CH)

(*) Notice: Subject to any disclaimer, the term of this patent is extended or adjusted under 35 U.S.C. 154(b) by 0 days.

(21) Appl. No.: 14/240,078

(22) PCT Filed: Aug. 14, 2012

(86) PCT No.: PCT/IB2012/054135
§ 371 (c)(1),
(2), (4) Date: Feb. 21, 2014

(87) PCT Pub. No.: WO2013/027154
PCT Pub. Date: Feb. 28, 2013

(65) Prior Publication Data
US 2014/0220137 A1   Aug. 7, 2014

(30) Foreign Application Priority Data

Aug. 22, 2011 (WO) .................. PCT/IB2011/053680

(51) Int. Cl.
| A01N 57/16 | (2006.01) |
| A01N 51/00 | (2006.01) |
| A01N 43/30 | (2006.01) |
| A01N 53/00 | (2006.01) |
| A01N 43/80 | (2006.01) |

(52) U.S. Cl.
CPC .............. *A01N 43/30* (2013.01); *A01N 43/80* (2013.01); *A01N 51/00* (2013.01); *A01N 53/00* (2013.01); *A01N 57/16* (2013.01)

(58) Field of Classification Search
CPC .................................................. A01N 25/00
See application file for complete search history.

(56) References Cited

U.S. PATENT DOCUMENTS

| 2003/0138500 A1* | 7/2003 | Parker et al. ................... 424/705 |
| 2005/0233986 A1* | 10/2005 | Clough ............................ 514/28 |
| 2012/0021911 A1* | 1/2012 | Majure et al. ................. 504/140 |

FOREIGN PATENT DOCUMENTS

WO   WO2010/101659   *   9/2010

OTHER PUBLICATIONS

Kaakeh, W., "Toxicity of imidacloprid to developmental stages of *Rhynchophorus ferrugineus* (Curculionidae: Coleoptera): Laboratory and field tests;" Crop Protection, 2006, vol. 25, pp. 432-439.

Dembilio, Oscar, et al., "Field efficacy in imidacloprid and Steinernema carpocapsae in chitosan formulation against the red palm weevil *Rhynchophorus ferrugineus* (Coleoptera: Curculionidae) in Phoenix canariensis," Pest Management Science, 2010, vol. 66, pp. 365-370.

Al-Shawaf, Abdul-Monem, A., "Toxicity of Certain Insecticides to *Rhynchophorus ferrugineus* in Relation to Acetylcholinesterase (AChE) and Monooxygenases (MFOs) Activities," Kingdom of Saudi Arabia, King Saud University, College of Food Sciences and Agriculture, 2004.

Llacer, E., et al., "Evaluation of the Efficacy of an Insecticidal Paint Based on Chlorpyrifos and Pyriproxyfen in a Microencapsulated Formulation Against *Rhychophorus ferrugineus* (Coleoptera: Curculionidae)," Journal of Economic Entomology, 2010, vol. 103(2), pp. 402-408.

Hernandez-Marante, D., et al., "Control of red palm weevil (*Rhynchophorus ferrugineus* Olivier) using trunk injections and foliar sprays," Boletin de Sanidad Vegetal, 2003, vol. 29, No. 4, pp. 563-573.

* cited by examiner

*Primary Examiner* — Scott Long
*Assistant Examiner* — Sarah Alawadi
(74) *Attorney, Agent, or Firm* — Duane Morris LLP; J. Rodman Steele, Jr.; Gregory M. Lefkowitz

(57) ABSTRACT

Synergistic composition able to rapidly and efficiently terminate *Rhynchophorus ferrugineus* infestation, in palms or other species suffering from this parasite. The composition comprises one or more among permethrin, cypermethrin, lambda-cyhalothrin; one or more among chlorpyrifos methyl, and chlorpyrifos ethyl; furthermore, benzisothiazolin-3-one, piperonyl butoxide, imidacloprid. The parasite dies shortly after contact with the product, infestation is terminated, and the palm remains protected against new attacks for a long time; the product is not toxic to the palm, on the contrary the plant recovers a level of health even higher than the initial one.

10 Claims, No Drawings

HIGH ACTIVITY ANTIPARASITIC COMPOSITION AGAINST *RHYNCHOPHORUS FERRUGINEUS*

CROSS-REFERENCE TO RELATED APPLICATIONS

This application is a §371 national stage entry of International Application No. PCT/IB2012/054135, filed Aug. 14, 2012, which claims priority to International Patent Application No. PCT/IB2011/053680 filed Aug. 22, 2011, the entire contents of which are incorporated herein by reference.

FIELD OF THE INVENTION

The present invention is in the field of pesticidal products. A new mixture of active ingredients able to completely terminate *Rhynchophorus ferrugineus* infestation in palms or other plants liable to this parasite is disclosed herein.

STATE OF THE ART

*Rhynchophorus ferrugineus* (generally known as red palm weevil) is a parasite native of south-eastern Asia and Melanesia, responsible for severe damage to palm plantations. Through the trade of infected palm individuals, the species reached the Arab Emirates in the eighties, and from here it spread in the Middle East and in the countries of the southern basin of the Mediterranean Sea; in 1994 it was reported in Spain and later, in 2006, in Corse and French Côte d'Azur. The first reporting in Italy occurred in 2004, on plants imported from Egypt; in 2005 the parasite was reported in Sicily and then quickly spreading towards the centre and north of the country. A recent study estimates that this parasite might bring to extinction the palms of the city of Rome within 2015 (A. Palumbo, Viavai, Dec. 1, 2008: "L'epidemia del punteruolo rosso diventa emergenza in città").

*Rhynchophorus ferrugineus* affects the most common ornamental palms of the Mediterranean such as *Phoenix canariensis*, and *Phoenix dactylifera*, but also species of economic interest such as coconut palm (*Cocos nucifera*) or oil palm (*Elaeis guineensis*). Other species on which attacks have been reported are *Areca catechu, Arenga pinnata, Borassus flabellifer, Calamus merillii, Caryota maxima, Caryota cumingii, Corypha gebanga, Corypha elata, Livistona decipiens, Metroxylon sagu, Oreodoxa regia, Phoenix sylvestris, Sabal umbraculifera, Trachycarpus fortunei, Washingtonia* spp. Occasionally, the parasite can attack *Agave americana* and *Saccharum officinarum*. Even species first considered immune from infestation, e.g. *Chamaerops humilis* (known as Mediterranean dwarf Palm, which produces a gummy secretion that prevents rooting of parasites) have been attacked (Boletin de Sanidad Vegetal, Plagas, 2000; 26(1), p.'73-'78).

*Rhynchophorus ferrugineus* infestation can be asymptomatic for a long time and become evident only at a late stage. The first symptoms are represented by an unusual change of the tree crown, which takes the splayed out appearance of an "open umbrella". Infestation can progress to more advanced stages, with progressive leaf loss and failure of the leaf rachis, until final collapse of the plant: at this point, parasite colonies leave the attacked plant migrating to an adjacent individual.

Control of *Rhynchophorus ferrugineus* is problematic due to various reasons. Adults easily move, and thus can overcome possible containment barriers, expanding infestation outbreaks. Traditional pesticidal products, normally efficient against other infesting species, were shown to be essentially inefficient against red palm weevil: in particular, at the present time it appears that there is no available product that kills the parasite shortly after contact, and that is able to completely terminate infestation without compromising viability and quality of the palm. Treatments are made even more difficult in that infestation often becomes evident only when the process is advanced, that is when the plant is already infested by a high number of differently distributed parasites: in these circumstances many parasite individuals survive the treatment, and the latter is never decisive. Another limit of these products is their toxicity to the plant: the resulting partial control of the infestation is associated with a decay of viability and ornamental appearance of the palm.

On the other hand, alternatives to classical pesticides are not sufficiently developed and/or not sufficiently efficient. For example, the employment of natural antagonists (auxiliary arthropods, nematodes, viruses, etc.) is still under study and, at the present time, no significant perspectives of application are available. The use of traps, widely experimented in different regions of Asia, of the Middle East and in Spain, resulted only partially efficient, and related technology must be refined to provide actual perspectives of success. Further, various experimental techniques were proposed, e.g. sterilized male technique, integrated pest management, use of dogs, however they remain far from a realistic perspective of commercial employment.

At the moment, the only efficient contrasting action remains the one based on prophylaxis, by intervening in a targeted way on infestation outbreaks with pruning and other targeted treatments; however, this involves the difficulty of constantly and carefully monitoring the state of the plantations, intervening where required on single plants or parts of them, which is not easily feasible and/or involves excessive costs.

Thus, there remains a urgent need for improved products and treatments to contrast red palm weevil infestation, being highly specific, so as to cause complete elimination of the parasite from the plant, possibly also via a single application; further, products and treatments are needed, being selective and/or efficient also at moderate doses so as to terminate infestation, while safeguarding the health of the palm; further, a product with high effectiveness characteristics is required, to save amounts of applied product, and/or to reduce treatment duration. Such needs become increasingly urgent in light of the persisting expansion of this infective epidemic, in particular in the Mediterranean area.

SUMMARY

The applicant has now identified a synergistic composition, based on a mixture of specific active ingredients, able to rapidly and efficiently terminate *Rhynchophorus ferrugineus* infestation, widely satisfying the above mentioned needs. The composition comprises one or more among permethrin, cypermethrin, lambda-cyhalothrin; one or more among chlorpyrifos methyl, and chlorpyrifos ethyl; furthermore, benzisothiazolin-3-one, piperonyl butoxide, imidacloprid. Said components, preferably present at the ratios recommended hereinafter, are admixed in a suitable amount of water and administered to the plant, preferably by watering or similar systems. The parasite dies within a few minutes upon contact with the product, infestation is terminated in a short time, and the palm remains long protected against new attacks; the product is not toxic to the palm, on the contrary the plant recovers high trophism, i.e. a health level even higher than the original one.

DETAILED DESCRIPTION

Object of the present invention is a pesticidal mixture active against *Rhynchophorus ferrugineus* comprising the following active ingredients: (a) one or more among permethrin, cypermethrin, lambda-cyhalothrin; (b) one or more among chlorpyrifos methyl and chlorpyrifos ethyl; (c) benzisothiazolin-3-one; (d) piperonyl butoxide; (e) imidacloprid.

The applicant observed that the components of such mixture work in a synergistic way producing different toxic effects on the parasite at issue, in particular: disinfectant, repellent, inhibitory on breathing, inhibitory on nervous transmission effects; only the simultaneous association of these effects resulted sufficient to kill the parasite; on the contrary, various partial mixtures of the same components, not able to exert these effects in a synergistic way, provided only a transient effect on the parasite, which after a period of stasis, became again able to grow and proliferate.

Components of the (a) group are active ingredients selected within the class of pyrethroids, known as insecticides, acaricides, and insect repellents with neurotoxic activity. Permethrin and cypermethrin are chlorinated derivatives; lambda-cyhalothrin is a chlorofluorinated derivative; these products are widely used in agriculture in particular in the treatment of cotton, wheat, corn. Components of the (a) group can be used individually or, preferably as a mixture thereof; particularly preferred is the ternary mixture of permethrin, cypermethrin and lambda-cyhalothrin. Components (a) taken together account preferably for $20\pm10\%$ by weight with respect to the total weight of (a)+(b)+(c)+(d)+(e) (hereinafter shortly indicated as "total of active ingredients"); more preferably, the single components of (a) are present in the following percentages by weight of the total of active ingredients:

(i) permethrin: $10.0\pm5.0\%$
(ii) cypermethrin: $7.8\pm5.0\%$
(iii) lambda-cyhalothrin: $2.5\pm1.0\%$.

Said active ingredients can also be used in a microincapsulated, commercially available form, e.g. microincapsulated permethrin 25/75 (Sepran), and/or microincapsulated cypermethrin 40/60 (Sepran).

Lambda-cyhalothrin is commercially available too (Syngenta, Karate, Scimitar).

Components of the (b) group are selected within the class of organophosphate insecticides; they are known acetylcholinesterase inhibitors, with low human and animal toxicity, used in agriculture for the treatment of crops such as corn, cotton, and fruit trees. Preferred for the invention is chlorpyrifos methyl (commercially available e.g. from Dow Agroscience), used in particular in a percentage of $34.4\pm10.0\%$ by weight of total of active ingredients. Said percentage is also usable in the case chlorpyrifos ethyl, or mixtures of chlorpyrifos ethyl and methyl are used, being referred to the total weight of the two products in that case.

Component (c), benzisothiazolin-3-one, is a biocide belonging to the class of isothiazolones. Microbicide and fungicide, it is predominantly employed as a preservative in emulsions, in particular for varnishes, adhesives, and similar products. It is preferably present in a percentage of $2.0\pm1.0\%$ by weight of total of active ingredients. The product is commercially available (e.g. Syngenta).

Component (d), piperonyl butoxide, is a semisynthetic derivative of safrole, an aspecific inhibitor of cytochrome p450 and esterase; it acts mainly by blocking detoxification mechanisms of the insect and making it more sensitive to insecticidal treatment. In the present invention it represents preferably $12.9\pm5.0\%$ by weight of total of active ingredients. The product is commercially available (e.g. Sepran).

Component (e), imidacloprid, is an insecticide of the neonicotinoid group, with neurotoxic effect. In the invention it preferably represents $30.4\pm10.0\%$ by weight of total of active ingredients. The product is commercially available (e.g. Nufarm).

A particularly preferred composition comprises, by weight of total of active ingredients: permethrin 10.0%; cypermethrin 7.8%; lambda-cyhalothrin 2,5%; chlorpyrifos methyl 34.4%; benzisothiazolin-3-one 2.0%; piperonyl butoxide 12.9%; imidacloprid: 30.4%.

The present mixtures, efficient as such in the treatment of *Rhynchophorus ferrugineus*, are conveniently integrated with common co-formulants useful in pesticidal compositions, such as preservatives, stabilizers, suspension agents, surfactants, diluents, fillers, etc., promoting administration in the desired form. Pesticidal compositions are thus obtained in a suitable form for marketing and administration; such compositions are part of the present invention.

If desired, other conventional active components can be optionally added to those described above in said groups (a)-(e); however, if present, their amounts are meant to be additional and not comprised in the percentages recommended for groups (a)-(e).

The mixture according to the present invention can be provided to the user in a dry (dry premix) or liquid form. When in a dry form, it is typically selected from powders, granulates, pellets, microcapsules, or similar forms. When in a liquid form, it is typically selected from solutions or suspensions.

Whatever the form of distribution and selling, the preferred final form for application on the field is the solution. In fact, it was observed that systemic administration to the plant of suitable amounts of solution, by watering or analogous systems, allows to uniformly establish efficient concentrations of pesticide in the body of the plant, which remain in situ for a long time; the red palm weevil attacking the body of the so treated plant comes in contact with the product and dies in a short time.

Hence, the mixture object of the invention is preferably provided to the user in a dry form or as a concentrated solution, in both cases to be diluted with a suitable amount of water at the time of use, up to the degree necessary for use. By way of example and without limitation, said concentrated solution can have a total concentration of active ingredients between 450 and 750 g/L, in particular between 550 and 650 g/L. The final degree of dilution can be varied according to the desired intensity of action. Advantageously, the composition remains active at very high degrees of dilution, thus maintaining high pesticide power while limiting the amount of active ingredient administered; preferably the diluted and ready to use solution has a total concentration of said active ingredients between 0.5 and 1.5 g/L, in particular between 1.0 and 1.4 g/L, ideally about 1.2 g/L; such solution can be obtained e.g. by diluting the previously exemplified concentrated solution. The final dilution can be further varied by the operator in charge of pest control for reasons of operating convenience, e.g. based on type of irrigator used, type of soil, etc.: as a general guide it is useful that a medium size infested plant receives a total of said active ingredients comprised between 10 and 30 g. (diluted in a suitable amount of water, e.g. 8-25 L) Such an amount of active ingredients, administered systemically by watering or similar systems, is sufficient to definitively kill parasites present on the plant, and/or new parasites that may attack it later. It is also possible to repeat the treatment one or more times at proper intervals, preferably three times a year; an ideal cycle is March-June- September. Particularly, in September the red palm weevil lays his eggs, so treatment in this month is quite important.

For the purpose of the invention, the above described mixture of active ingredients is used for pesticidal aims. In particular, it finds useful application in the treatment and/or prophylaxis of *Rhynchophorus ferrugineus* infestations. The term "and/or" refers to the case when the product is applied to several plants, for example a lot or plantation, wherein some individuals are already infected and need an efficient treatment, while other adjacent individuals are not contaminated yet but, being at risk, need prophylaxis. The above defined amounts and concentrations can be equally applied to treatment and/or prophylaxis.

The mixture is typically administered to palms, representing the preferred substrate on which *Rhynchophorus ferrugineus* acts. Therefore all the known species of palm can be treated according to the invention, as well as any other plant liable to this parasite. Non limiting examples of plants that can be treated are: *Phoenix canariensis, Phoenix dactylifera, Cocos nucifera, Elaeis guineensis, Areca catechu, Arenga pinnata, Borassus flabellifer, Calamus merillii, Caryota maxima, Caryota cumingii, Corypha gebanga, Corypha elata, Livistona decipiens, Metroxylon sagu, Oreodoxa regia, Phoenix sylvestris, Sabal umbraculifera, Trachycarpus fortunei, Washingtonia* spp., *Agave americana, Saccharum officinarum, Chamaerops humilis*.

The present treatment proved to be non-toxic to the health of the plant. In particular, it was surprisingly observed that numerous palms treated with the product of the invention, after elimination of infestation, showed in some cases a second flowering: this demonstrates not only the lack of toxicity of the product at the used doses and the recovery of the palm functionality prior to infestation, but also a higher general trophism; the latter turns into in improved health and resistance to possible new attacks, as well as improved ornamental effect.

The invention is hereinafter illustrated in a non-limiting way by the following examples.

EXPERIMENTAL PART

Example 1

A 580.90 g mixture was prepared from the following amounts of active ingredients: 14.7 g pure lambda-cyhalothrin; 12 g benzisothiazolin-3-one; 201.2 g pure chlorpyrifos methyl; 59 g microincapsulated permethrin 25/75; 46 g microincapsulated cypermethrin 40/60; 76 g piperonyl butoxide; 178 g pure imidacloprid. The product was dissolved in water up to the volume of 1 litre, obtaining a concentrated solution.

The concentrated solution was then diluted 1/500, obtaining a ready to use solution; 15 litres of such solution were administered by watering to a palm (*Phoenix canariensis*) of about 5 years of age with about 2 meter long leaves, infested by *Rhynchophorus ferrugineus*. The solution was poured on the ground around the palm, and further on the palm trunk and leaves.

After about half an hour, the surface of the palm was found free from living parasites; only dead parasites were found, on the soil around the plant or occasionally on the plant itself. As a precaution, the treatment was repeated every 40 days for prophylactic purposes. The plant recovered the initial state of health, also showing in some cases unexpected signs of new flowering. The treatment was extended to a whole lot of sixty palms (twenty *Phoenix canariensis*, six *Chamaerops humilis*, twenty nine mixed washingtonias of the filifera and robusta types, four *Trachycarpus fortunei* palms, one *Phoenix roebelenii*), and thirteen cycas, confirming the above disclosed result.

Example 2

A ready-to-use pesticidal solution for direct administration to palm trees was prepared, having the following concentrations of active agents: 0.02940 g/L lambda-cyhalothrin; 0.02400 g/L benzisothiazolin-3-one; 0.40240 g/L chlorpyrifos methyl; 0.11800 g/L permethrin; 0.9200 g/L cypermethrin; 0.15200 g/L piperonyl butoxide; 0.35600 g/L imidacloprid. The overall active principles concentration was thus 1.1738 g/L. 18 L of this solution were administered to a palm of about 13 years of age infested by *Rhynchophorus ferrugineus*; using a pump with terminal sprayer, the solution was sprayed on the ground around the palm, and further on the palm (trunk and leaves). In about 30 minutes, the surface of the palm was found free from living parasites; only dead parasites were found, on the soil around the plant or occasionally on the plant itself. The treatment was performed three times during one year (March, June, September): as a result, no further infestation took place, and the treatment restored the initial state of health of the palm.

Example 3

The initial treatment of example 2 was repeated on different palms using the same pesticide solution, but diluted to an overall concentration of active principles of 1.00, 0.90, 0.75 g/L, respectively. All these solutions remained highly active on *Rhynchophorus ferrugineus*, obtaining their total mortality within 4 hour, as detailed in the following table:

| Overall AP concentration g/L | Mortality % | Time min |
| --- | --- | --- |
| 1.17 | 100 | <30 |
| 1.00 | 100 | 90 |
| 0.90 | 100 | 150 |
| 0.75 | 100 | 210 |

Example 4

In order to check if the pesticide is active via systemic circulation in the palm, the following experiment was performed. An isolated group of *Rhynchophorus ferrugineus* were fed with newborn leaves from a palm previously treated with the present pesticide composition, and the effect on their viability was studied; the chosen leaves were those born long after the treatment, therefore their possible pesticidal activity indicates that the pesticide was absorbed via systemic circulation.

A few hours after being fed, the parasites developed signs of malaise, and they all died within the same day, as detailed in the following table:

| | Time | | | | | |
| --- | --- | --- | --- | --- | --- | --- |
| | 1 hr | 2 hr | 4 hr | 6 hr | 8 hr | 10 hr |
| Mortality | 0% | 5% | 30% | 75% | 95% | 100% |

This confirmed that the pesticide is absorbed systemically by the palm, and affords long-lasting protection against *Rhynchophorus ferrugineus*.

Example 5

A series of reference compositions containing only part of the components (a)-(e) object of the invention, were prepared and directly tested on thirty individuals of *Rhynchophorus ferrugineus*, the parasite was wetted with the composition by using a spray.

After the treatment, such individuals were observed to analyze possible toxic effects and residual viability of the parasite.

Composition R1:

Mixture of microincapsulated permethrin 25/75+pure chlorpyrifos methyl+pure piperonyl butoxide.

In various tests with this mixture, red palm weevil showed difficulty of breathing and could not fly. However, about 2 hours after treatment the parasite recovered viability and, over 2 days, recovered its original viability. Such result was considered inadequate for an efficient treatment of an infested plant or plantation.

Composition R2:

Mixture of pure lambda-cyhalothrin+microincapsulated cypermethrin 40/60+pure chlorpyrifos methyl.

In various tests with this mixture, red palm weevil showed difficulty of movement for about 3 hours from treatment. Afterwards, the parasite gradually recovered viability and, over 2 days, recovered its original viability, including the ability to fly. Such result was considered inadequate for an efficient treatment of an infested plant or plantation.

Composition R3:

Mixture of benzisothiazolin-3-one+pure chlorpyrifos methyl+pure piperonyl butoxide.

In various tests with this mixture, red palm weevil showed enlargement of the abdomen and signs of respiratory difficulty. Death, presumably due to dehydration, occurred only after a long time, i.e. about one week after treatment. Such result was considered inadequate for an efficient treatment of an infested plant or plantation.

Composition R4:

Mixture of pure lambda-cyhalothrin+pure cypermethrin+pure imidacloprid.

In various tests with this mixture, red palm weevil showed evident signs of lack of motorial coordination for about 1 week. Afterwards, in 2-3 weeks, the parasite partly recovered its original viability, never recovering initial coordination and completeness of movement. Such result was considered inadequate for an efficient treatment of an infested plant or plantation.

Said tests R1-R4 showed an unsatisfactory degree of activity against red palm weevil by partial mixtures of insecticides; such data are surprising, being the single components generally considered self-sufficient as pesticides. This demonstrates, on one side the strong resistance of the red palm weevil, and on the other side the importance of the result obtained with the mixture according to the invention, consisting in the complete pest elimination from plants suffering from red palm weevil, as proven by field experiments described in example 1.

The invention claimed is:

1. A pesticidal mixture comprising the following active ingredients:
    (a) permethrin: 10.0±5.0%,
    (b) cypermethrin: 7.8±5.0%,
    (c) lambda-cyhalothrin: 2.5±1.0%,
    (d) chlorpyrifos methyl and/or ethyl: 34.4±10.0%,
    (e) benzisothiazolin-3-one: 2.0±1.0%,
    (f) piperonyl butoxide: 12.9±5.0%, and
    (g) imidacloprid: 30.4±10.0%;
    wherein all percentages for ingredients (a)-(g) are by weight based on the total weight of active ingredients (a)-(g).

2. Mixture according to claim 1, wherein one or more among said active ingredients is in a microincapsulated form.

3. Mixture according to claim 1, further comprising co-formulants useful in pesticidal compositions.

4. Mixture according to claim 1, in a dry or liquid form.

5. Dry mixture according to claim 4, in the form of a powder, granulate, pellet, microcapsule.

6. Liquid mixture according to claim 4, in the form of a ready-to-use diluted solution, or as a concentrated solution to dilute before use.

7. Mixture according to claim 6, wherein said ready to use solution has a total concentration of said active ingredients comprised between 0.5 and 1.5 g/L.

8. Mixture according to claim 6, wherein said concentrated solution has a total concentration of said active ingredients comprised between 450 and 750 g/L.

9. The mixture according to claim 6, wherein said ready to use solution has a total concentration of said active ingredients comprised between 1.0 and 1.4 g/L.

10. The mixture according to claim 6, wherein said concentrated solution has a total concentration of said active ingredients comprised between 550 and 650 g/L.

* * * * *